(12) United States Patent
Le Couedic et al.

(10) Patent No.: US 7,641,673 B2
(45) Date of Patent: Jan. 5, 2010

(54) FLEXIBLE LINKING PIECE FOR STABILISING THE SPINE

(75) Inventors: Regis Le Couedic, Bordeaux (FR); Denis Pasquet, Pessac (FR)

(73) Assignee: Zimmer Spine, S.A.S., Bordeaux (FR)

( * ) Notice: Subject to any disclaimer, the term of this patent is extended or adjusted under 35 U.S.C. 154(b) by 12 days.

(21) Appl. No.: 10/333,881

(22) PCT Filed: Jul. 25, 2001

(86) PCT No.: PCT/FR01/02426

§ 371 (c)(1),
(2), (4) Date: Jan. 24, 2003

(87) PCT Pub. No.: WO02/07622

PCT Pub. Date: Jan. 31, 2002

(65) Prior Publication Data

US 2004/0049189 A1      Mar. 11, 2004

(51) Int. Cl.
*A61B 17/70* (2006.01)
(52) U.S. Cl. .................................... 606/259
(58) Field of Classification Search .............. 606/60, 606/61, 72, 73; 623/11.11, 16.11, 17.11, 623/17.12, 17.13, 17.14–17.16, 22.13, 22.14, 623/21.11, 21.15; 188/379–380; 267/33–35, 267/64.16, 64.17, 136, 140, 152, 153
See application file for complete search history.

(56) References Cited

U.S. PATENT DOCUMENTS

| | | | |
|---|---|---|---|
| 2,515,366 A | 7/1950 | Zublin | |
| 2,585,207 A | 2/1952 | Zublin | |
| 2,649,092 A | 8/1953 | Wallace | |
| 3,669,133 A | 6/1972 | Hyman | |
| 4,328,839 A | 5/1982 | Lyons | |
| 4,648,388 A | 3/1987 | Steffee | |

(Continued)

FOREIGN PATENT DOCUMENTS

EP      0381588      8/1990

(Continued)

OTHER PUBLICATIONS

International Search Report issued in PCT/FR2001/02426, mailed Oct. 30, 2001, Spine Next, 6 pages (with translation).

(Continued)

*Primary Examiner*—Anu Ramana
(74) *Attorney, Agent, or Firm*—Sprinkle IP Law Group

(57) ABSTRACT

The invention relates to a connecting member for maintaining the spacing between at least two anchor members screwed into vertebrae. It comprises two rigid rod-forming parts (12, 14) made of a first material and each having a fixing, first portion (16, 18) adapted to be fixed into an anchor member and a fastening, second portion (20, 22), said rods (12, 14) being aligned with each other and said fastening portions (20, 22) facing each other, and a connecting body (24) made of a second material which is more elastically deformable than said first material and which interconnects said rigid parts (12, 14) by means of the facing fastening portions (20, 22) so that said connecting body (24) is able to deform elastically, whereby the vertebrae, which are held spaced from each other, are movable relative to each other.

11 Claims, 2 Drawing Sheets

U.S. PATENT DOCUMENTS

| | | | |
|---|---|---|---|
| 4,697,582 A | 10/1987 | William | |
| 4,743,260 A | 5/1988 | Burton | |
| 4,763,644 A | 8/1988 | Webb | |
| 4,773,402 A | 9/1988 | Asher et al. | |
| 4,805,602 A | 2/1989 | Puno et al. | |
| 4,887,596 A | 12/1989 | Sherman | |
| 4,892,552 A | 1/1990 | Ainsworth | |
| 4,917,700 A | 4/1990 | Aikins | |
| 4,932,975 A * | 6/1990 | Main et al. | 623/17.12 |
| 4,946,378 A * | 8/1990 | Hirayama et al. | 623/17.16 |
| 4,950,269 A | 8/1990 | Gaines, Jr. | |
| 5,002,576 A | 3/1991 | Fuhrmann et al. | |
| 5,011,497 A * | 4/1991 | Persson et al. | 623/23.41 |
| 5,034,011 A | 7/1991 | Howland | |
| 5,092,866 A | 3/1992 | Breard et al. | |
| 5,102,412 A | 4/1992 | Rogozinski | |
| 5,129,388 A | 7/1992 | Vignaud et al. | |
| 5,154,718 A | 10/1992 | Cozad et al. | |
| 5,176,708 A | 1/1993 | Frey et al. | |
| 5,181,917 A | 1/1993 | Rogozinski | |
| 5,217,450 A | 6/1993 | Pryor et al. | |
| 5,282,863 A | 2/1994 | Burton | |
| 5,334,203 A | 8/1994 | Wagner | |
| 5,368,594 A | 11/1994 | Martin et al. | |
| 5,375,823 A | 12/1994 | Navas | |
| 5,413,576 A | 5/1995 | Rivard | |
| 5,413,602 A | 5/1995 | Metz-Stavenhagen | |
| 5,415,661 A | 5/1995 | Holmes | |
| 5,423,816 A | 6/1995 | Lin | |
| 5,423,817 A | 6/1995 | Lin | |
| 5,423,819 A | 6/1995 | Small | |
| 5,456,722 A | 10/1995 | McLeod et al. | |
| 5,480,401 A | 1/1996 | Navas | |
| 5,488,761 A | 2/1996 | Leone | |
| 5,496,318 A | 3/1996 | Howland et al. | |
| 5,508,093 A | 4/1996 | Mehdorn | |
| 5,540,688 A * | 7/1996 | Navas | 606/61 |
| 5,562,660 A | 10/1996 | Grob | |
| 5,562,737 A | 10/1996 | Graf | |
| 5,591,165 A | 1/1997 | Jackson | |
| 5,609,634 A | 3/1997 | Voydeville | |
| 5,611,800 A * | 3/1997 | Davis et al. | 606/250 |
| 5,616,142 A | 4/1997 | Yuan et al. | |
| 5,645,599 A | 7/1997 | Samani | |
| 5,658,286 A | 8/1997 | Sava | |
| 5,672,175 A | 9/1997 | Martin | |
| 5,725,582 A | 3/1998 | Bevan et al. | |
| 5,733,284 A | 3/1998 | Martin | |
| 5,782,831 A | 7/1998 | Sherman et al. | |
| 5,888,201 A | 3/1999 | Stinson | |
| RE36,221 E | 6/1999 | Breard et al. | |
| 5,928,233 A | 7/1999 | Apfelbaum | |
| 5,928,284 A * | 7/1999 | Mehdizadeh | 623/17.13 |
| 5,951,555 A | 9/1999 | Rehak et al. | |
| 5,961,516 A * | 10/1999 | Graf | 606/61 |
| 5,982,233 A | 11/1999 | Hellmark et al. | |
| 5,984,923 A | 11/1999 | Breard | |
| 6,053,922 A | 4/2000 | Krause et al. | |
| 6,080,157 A | 6/2000 | Cathro et al. | |
| 6,162,223 A | 12/2000 | Orsak et al. | |
| 6,206,882 B1 | 3/2001 | Cohen | |
| 6,241,730 B1 * | 6/2001 | Alby | 606/61 |
| 6,248,106 B1 | 6/2001 | Ferree | |
| 6,267,764 B1 | 7/2001 | Elberg | |
| 6,270,910 B1 | 8/2001 | Jaeger et al. | |
| 6,290,700 B1 | 9/2001 | Schmotzer | |
| 6,293,949 B1 | 9/2001 | Justis et al. | |
| 6,296,643 B1 | 10/2001 | Hopf et al. | |
| 6,306,136 B1 | 10/2001 | Baccelli | |
| 6,312,431 B1 | 11/2001 | Asfora | |
| 6,337,142 B2 | 1/2002 | Harder et al. | |
| 6,352,557 B1 | 3/2002 | Ferree | |
| 6,419,702 B1 | 7/2002 | Ferree | |
| 6,440,169 B1 | 8/2002 | Elberg et al. | |
| 6,447,518 B1 | 9/2002 | Krause et al. | |
| 6,447,546 B1 | 9/2002 | Bramlet et al. | |
| 6,500,178 B2 | 12/2002 | Zucherman et al. | |
| 6,551,321 B1 | 4/2003 | Burkinshaw | |
| 6,554,831 B1 | 4/2003 | Rivard et al. | |
| 6,582,468 B1 * | 6/2003 | Gauchet | 623/17.16 |
| 6,585,738 B1 | 7/2003 | Mangione et al. | |
| 6,602,293 B1 | 8/2003 | Biermann | |
| 6,610,062 B2 | 8/2003 | Bailey et al. | |
| 6,610,079 B1 | 8/2003 | Li et al. | |
| 6,616,669 B2 | 9/2003 | Ogilvie et al. | |
| 6,626,904 B1 | 9/2003 | Jammet et al. | |
| 6,626,944 B1 | 9/2003 | Taylor | |
| 6,648,885 B1 | 11/2003 | Friesem | |
| 6,652,585 B2 | 11/2003 | Lange | |
| 6,656,184 B1 | 12/2003 | White et al. | |
| 6,679,883 B2 | 1/2004 | Hawkes et al. | |
| 6,695,842 B2 | 2/2004 | Zucherman et al. | |
| 6,706,044 B2 | 3/2004 | Kuslich et al. | |
| 6,723,335 B1 | 4/2004 | Ranieri | |
| 6,733,534 B2 | 5/2004 | Sherman | |
| 6,749,614 B2 | 6/2004 | Teitelbaum | |
| 6,752,831 B2 | 6/2004 | Sybert et al. | |
| 6,761,719 B2 | 7/2004 | Justis et al. | |
| 6,761,720 B1 | 7/2004 | Senegas | |
| 6,783,527 B2 | 8/2004 | Drewry et al. | |
| 6,802,844 B2 | 10/2004 | Ferree | |
| 7,413,576 B2 | 10/2004 | Sybert et al | |
| 6,852,128 B2 | 2/2005 | Lange | |
| 6,875,212 B2 | 4/2005 | Shaolian | |
| 6,899,713 B2 | 5/2005 | Shaolian et al. | |
| 6,899,716 B2 | 5/2005 | Cragg | |
| 6,921,403 B2 | 7/2005 | Cragg et al. | |
| 6,946,000 B2 | 9/2005 | Senegas et al. | |
| 6,964,667 B2 | 11/2005 | Shaolian | |
| 6,966,910 B2 | 11/2005 | Ritland | |
| 6,986,771 B2 | 1/2006 | Paul et al. | |
| 6,987,011 B1 | 1/2006 | Reid et al. | |
| 6,989,011 B2 | 1/2006 | Paul | |
| 6,991,632 B2 | 1/2006 | Ritland | |
| 7,008,424 B2 | 3/2006 | Teitelbaum | |
| 7,018,379 B2 | 3/2006 | Drewry et al. | |
| 7,029,475 B2 | 4/2006 | Panjabi | |
| 7,125,410 B2 | 10/2006 | Freudiger | |
| 7,137,985 B2 | 11/2006 | Jahng | |
| 7,175,626 B2 | 2/2007 | Neff | |
| 7,329,258 B2 | 2/2008 | Studer | |
| 2002/0035366 A1 | 3/2002 | Walder | |
| 2002/0082598 A1 | 6/2002 | Teitelbaum | |
| 2002/0082698 A1 | 6/2002 | Parenteau et al. | |
| 2002/0120272 A1 | 8/2002 | Yuan et al. | |
| 2002/0138077 A1 | 9/2002 | Ferree | |
| 2003/0069639 A1 | 4/2003 | Sander et al. | |
| 2003/0083657 A1 | 5/2003 | Drewry et al. | |
| 2003/0109880 A1 | 6/2003 | Shirado et al. | |
| 2003/0171749 A1 | 9/2003 | Le Couedic et al. | |
| 2003/0191470 A1 | 10/2003 | Ritland | |
| 2004/0002708 A1 | 1/2004 | Ritland | |
| 2004/0015166 A1 | 1/2004 | Gorek | |
| 2004/0049190 A1 | 3/2004 | Biedermann | |
| 2004/0073215 A1 | 4/2004 | Carli | |
| 2004/0082954 A1 | 4/2004 | Teitelbaum et al. | |
| 2004/0097931 A1 | 5/2004 | Mitchell | |
| 2004/0106995 A1 | 6/2004 | Le Couedic et al. | |
| 2004/0138662 A1 | 7/2004 | Landry et al. | |
| 2004/0143265 A1 | 7/2004 | Landry | |
| 2004/0167625 A1 | 8/2004 | Beyar et al. | |
| 2004/0172022 A1 | 9/2004 | Landry | |
| 2005/0065514 A1 | 3/2005 | Studer | |
| 2005/0075634 A1 | 4/2005 | Zucherman et al. | |

| | | | |
|---|---|---|---|
| 2005/0085815 A1 | 4/2005 | Harms et al. | |
| 2005/0125063 A1 | 6/2005 | Matge et al. | |
| 2005/0149022 A1 | 7/2005 | Shaolian | |
| 2005/0149023 A1 | 7/2005 | Ritland | |
| 2005/0154390 A1 | 7/2005 | Biedermann et al. | |
| 2006/0009768 A1 | 1/2006 | Ritland | |
| 2006/0084993 A1 | 4/2006 | Landry et al. | |
| 2006/0142758 A1 | 6/2006 | Petit | |
| 2006/0142761 A1 | 6/2006 | Landry et al. | |
| 2006/0241640 A1 | 10/2006 | Briard et al. | |
| 2007/0016193 A1 | 1/2007 | Ritland | |
| 2007/0083201 A1 | 4/2007 | Jones | |
| 2007/0129729 A1 | 6/2007 | Petit et al. | |
| 2007/0179503 A1 | 8/2007 | Ferree | |
| 2007/0198088 A1 | 8/2007 | Biedermann et al. | |
| 2008/0039843 A1 | 2/2008 | Abdou | |
| 2008/0039943 A1 | 2/2008 | Le Couedic | |
| 2008/0140076 A1 | 6/2008 | Jackson | |
| 2008/0147122 A1 | 6/2008 | Jackson | |
| 2008/0262552 A1 | 10/2008 | Kim | |
| 2008/0294198 A1 | 11/2008 | Jackson | |
| 2009/0005817 A1 | 1/2009 | Friedrich et al. | |
| 2009/0012562 A1 | 1/2009 | Hestad | |
| 2009/0099606 A1 | 4/2009 | Hestad | |

FOREIGN PATENT DOCUMENTS

| | | |
|---|---|---|
| EP | 0478470 | 4/1992 |
| EP | 0516567 | 12/1992 |
| EP | 0576379 | 12/1993 |
| EP | 0611554 | 8/1994 |
| EP | 0649293 | 4/1995 |
| EP | 0 669109 B1 | 8/1995 |
| EP | 0667127 | 8/1995 |
| EP | 0677277 | 10/1995 |
| EP | 0768843 | 4/1997 |
| EP | 1054638 | 11/2000 |
| EP | 1138268 | 10/2001 |
| EP | 1239785 | 9/2002 |
| EP | 1299042 | 4/2003 |
| EP | 1303224 | 4/2003 |
| EP | 1303225 | 4/2003 |
| EP | 1281361 | 5/2003 |
| EP | 1364622 | 11/2003 |
| EP | 1388323 | 2/2004 |
| EP | 1399078 | 3/2004 |
| EP | 1 523 949 B1 | 4/2005 |
| EP | 1815812 | 8/2007 |
| FR | 2 676 911 | 12/1992 |
| FR | 2697428 | 6/1994 |
| FR | 2715057 | 7/1995 |
| FR | 2728158 | 6/1996 |
| FR | 2 730 405 | 8/1996 |
| FR | 2735351 | 12/1996 |
| FR | 2 755 844 | 5/1998 |
| FR | 2774581 | 8/1999 |
| FR | 2775583 | 9/1999 |
| FR | 2799949 | 4/2001 |
| FR | 2817461 | 6/2002 |
| FR | 2844180 | 3/2004 |
| FR | 2845268 B1 | 4/2004 |
| FR | 2845587 | 4/2004 |
| FR | 2867057 | 9/2005 |
| FR | 2890850 | 3/2007 |
| GB | 2269753 A | 2/1994 |
| GB | 2320198 A | 6/1998 |
| GB | 2382304 A | 5/2003 |
| NL | 7610576 | 3/1978 |
| WO | WO9013265 | 11/1990 |
| WO | WO94026192 | 11/1994 |
| WO | WO95005783 | 3/1995 |
| WO | WO 9519149 | 7/1995 |
| WO | WO96015729 | 5/1996 |
| WO | WO96041582 | 12/1996 |
| WO | WO97009940 | 3/1997 |
| WO | WO97032533 | 9/1997 |
| WO | WO 9905980 | 2/1999 |
| WO | WO9940866 | 8/1999 |
| WO | WO0139678 | 6/2001 |
| WO | WO0149192 | 7/2001 |
| WO | WO0164144 | 9/2001 |
| WO | WO 0207621 | 1/2002 |
| WO | WO 0207622 | 1/2002 |
| WO | WO0217803 | 3/2002 |
| WO | WO0243603 | 6/2002 |
| WO | WO02067792 | 9/2002 |
| WO | WO02071960 | 9/2002 |
| WO | WO02102259 | 12/2002 |
| WO | WO03007828 | 1/2003 |
| WO | WO03015645 | 2/2003 |
| WO | WO03015646 | 2/2003 |
| WO | WO03047441 | 6/2003 |
| WO | WO03047442 | 6/2003 |
| WO | WO03077806 | 9/2003 |
| WO | WO03094699 | 11/2003 |
| WO | WO/2004/024011 A1 | 3/2004 |
| WO | WO2004017817 | 3/2004 |
| WO | WO2004034916 | 4/2004 |
| WO | WO2004039283 | 5/2004 |
| WO | WO2004084743 | 10/2004 |
| WO | WO2004091413 | 10/2004 |
| WO | WO2004098423 | 11/2004 |
| WO | WO2004098452 | 11/2004 |
| WO | WO 2005118015 | 12/2005 |

OTHER PUBLICATIONS

International Preliminary Report on Patentability issued in PCT/FR01/02426 mailed Oct. 22, 2002, Spine Next, 10 pages (with translation).
International Search Report issued in PCT/FR2005/001280, mailed Nov. 7, 2005, Abbott Spine, 6 pages (with translation).
International Preliminary Report on Patentability and Written Opinion issued in PCT/FR05/001280 mailed Nov. 29, 2006, Spine Next, 13 pages (with translation).
Office Action issued in U.S. Appl. No. 11/597,120, mailed Sep. 30, 2008, Le Couedic, 7 pages.
Office Action issued in U.S. Appl. No. 11/597,120, mailed Feb. 23, 2009, Le Couedic, 9 pages.
Bannon et al. "Titanium Alloys for Biomaterial Application: An Overview," Titanium Alloys in Surgical Implants, ASTM STP 796, Luckey et al., Eds., American Society for Testing and Materials, 1983. pp. 7-15.
IPRP mailed Sep. 18, 2007 PCT/US2006/008232.
Office Action issued in U.S. Appl. No. 11/082,297, mailed Apr. 24, 2009, Foster et al., 11 pages.
Office Action issued in U.S. Appl. No. 11/082,297, mailed Oct. 20, 2008, Foster et al., 18 pages.
Office Action issued in U.S. Appl. No. 11/082,297, mailed Mar. 20, 2008, Foster et al., 15 pages.
Office Action issued in U.S. Appl. No. 11/597,120, mailed Jun. 10, 2009 Le Couedic, 11 pages.
Office Action issued in U.S. Appl. No. 10/333,284 mailed Dec. 14, 2004, Le Couedic, 7 pages.
Office Action issued in U.S. Appl. No. 10/333,284 mailed Aug. 23, 2005, Le Couedic, 8 pages.
Office Action issued in U.S. Appl. No. 10/333,284 mailed Mar. 24, 2006, Le Couedic, 8 pages.
Table of Contents of "Titanium Alloys in Surgical Implants," Luckey et al., Eds., American Society for Testing and Materials, 1983.
International Search Report mailed for PCT/US2009/038977 mailed Jul. 22, 2009.
French Preliminary Search Report dated Jan. 12, 2005 in Patent Application No. FR 0405611.

* cited by examiner

FLEXIBLE LINKING PIECE FOR STABILISING THE SPINE

FIELD OF THE INVENTION

The present invention relates to a connecting member for maintaining the spacing between at least two anchor members which are interconnected by said connecting member.

BACKGROUND OF THE INVENTION

Fields of application of the invention include stabilization and arthrodesis of segments of the vertebral column in degenerative pathologies of the spine.

Systems for stabilizing the vertebral column by bracing at least two consecutive vertebrae by means of anchor members fixed into said vertebrae and connected by rigid connecting rods are well known in the art. Systems of this kind are generally coupled systems such that two consecutive vertebrae are interconnected by two substantially parallel rods fixed one on each side of the spinous processes. The anchor members are screwed into the posterior portions of the vertebrae and pass through the pedicles and a substantial portion of the vertebral bodies and therefore provide a fixed and durable connection.

The above stabilizing systems are routinely used to consolidate several consecutive vertebrae. Thus the vertebrae are interconnected by rigid rods over a substantial length of the vertebral column. Such assemblies hold the vertebrae correctly relative to each other; however, they considerably stiffen the spine in terms of bending. It has been shown that a more flexible stabilizing system, which confers greater relative mobility on the vertebrae, is beneficial in some pathologies.

BRIEF SUMMARY OF THE INVENTION

A first object of the present invention is to provide a connecting member for maintaining the spacing of existing anchor members while at the same time allowing relative mobility of said anchor members.

To achieve the above object, a connecting member in accordance with the invention, adapted to maintain the spacing between at least two anchor members screwed into vertebrae, comprises at least two rigid rod-forming parts made of a first material and each having a fixing, first portion adapted to be fixed into an anchor member and a fastening, second portion, said rods being aligned with each other and said fastening portions facing each other, and a connecting body that is made entirely from a second material that is more elastically deformable than said first material and interconnects the facing fastening portions of said rigid parts so that said connecting body is able to deform elastically, whereby the vertebrae, which are held spaced from each other, are movable relative to each other.

Thus a feature of the connecting member lies in the way the two rigid parts are fastened together by means of an elastically deformable connecting body which imparts relative mobility to the rigid parts when under stress, with the reaction force to the stress being proportional, within certain limits, to the deformation of the connecting body. As a result, the connecting member can be bent by stresses in directions that are not parallel to the axis of the connecting member; it can also be stretched or contracted by opposing forces acting parallel to the axis of the connecting member.

Consequently, the two anchor members, when at rest, are interconnected by the connecting member with its fixing portions fastened to the anchor members, and can be moved relative to each other by forces proportional to the movement.

Said rigid parts are preferably mechanically connected together by a single connecting body providing the whole of said mechanical connection. In this way a single member provides the connection between the rigid parts at the same time as controlling relative movement of the rigid parts. Also, in a particular embodiment, said connecting body consists entirely of a single second material to simplify assembly and to impart homogeneous mechanical properties to it.

The connecting member of the invention advantageously has $\underline{n}$ rigid parts with n−1 connecting bodies disposed between them along the longitudinal axis of said member, each rigid part situated between two connecting bodies having one fixing, first portion and two fastening, second portions, there being one fastening, second portion at each end of said fixing, first portion, and said fastening, second portions being connected respectively to said two connecting bodies, and the rigid parts at the two ends of said member advantageously have respective single fastening, second portions connected to the connecting bodies, whereby said connecting member is adapted to interconnect $\underline{n}$ anchor members.

Thus, by virtue of this feature, the connecting member maintains the spacing between all the anchor members that it interconnects, each of which can be fixed to a respective vertebra, to align them. Each rigid part is fixed to an anchor member and, between successive anchor members, there is a connecting body that interconnects the two fastening portions. Thus a single connecting member stabilizes several vertebrae, which reduces the time to assemble the stabilizing system as a whole and consequently the operating time. Also, by virtue of this feature, the connecting member stabilizes several consecutive vertebrae by connecting them together, while at the same time making them highly flexible and conferring on them a high degree of relative compressibility in the longitudinal direction.

In a preferred embodiment of the invention each of said fastening portions of said rigid parts that said connecting body interconnects has a fastening wall to which said connecting body is adapted to adhere. Thus no additional fixing member is needed and the adhesive properties of the second material to the fastening wall are sufficient to connect them.

In one particular embodiment of the invention, said fastening wall has openings adapted to cooperate with asperities on said connecting body to increase the surface area of contact between said wall and said body.

Obviously, providing openings in a wall increases the surface area of that wall, which increases the contact area between the two materials if one of the materials can be molded onto the wall of the other material. The increase in contact area increases the connecting forces between said connecting body and said fastening portions. Also, the static friction forces of the material of the connecting member on said two members are increased in a corresponding manner and these forces are added to the connecting forces.

Said second material of which said connecting body is made is advantageously obtained by polymerization. In this way, the connecting body can easily be hot molded onto the fastening walls if the material is polymerized beforehand, or it can be formed in situ if the rate of polymerization of the monomers constituting said second material is sufficiently low to provide the time necessary for completing the assembly.

In a preferred embodiment of the invention said first material of which said rigid parts are made is a titanium alloy. It is therefore easy to form openings in said fastening wall to which said connecting body is able to adhere.

In another preferred embodiment of the invention, the section of said rigid rod-forming parts is circular, which facilitates the manufacture of the member. Also, if prior art circular section connecting rods are to be replaced by connecting rods of the invention without making it necessary to replace the anchor members, it is necessary for said rigid parts to have sections identical to the sections of the prior art connecting rods.

The present invention also provides a vertebral stabilization system for fastening together at least two vertebrae each having a median plane substantially perpendicular to the axis of the spine of which they form a part and a posterior wall defining a posterior median plane of said spine, said system comprising at least two anchor members each adapted to be fixed into the posterior wall of a respective vertebra so that a line which intersects said two anchor members is substantially parallel to said axis of the spine, which system further comprises at least one connecting member of the invention whose two rigid parts are adapted to interconnect said two anchor members so that the axis of said connecting member is substantially parallel to said axis of the spine, whereby said vertebrae, which are interconnected via their posterior portions, present relative mobility along said axis of said spine.

BRIEF DESCRIPTION OF THE DRAWINGS

Other features and advantages of the invention will emerge on reading the following description of particular embodiments of the invention, which is given by way of non-limiting example and with reference to the accompanying drawings, in which.

DETAILED DESCRIPTION OF THE INVENTION

Figure 1:
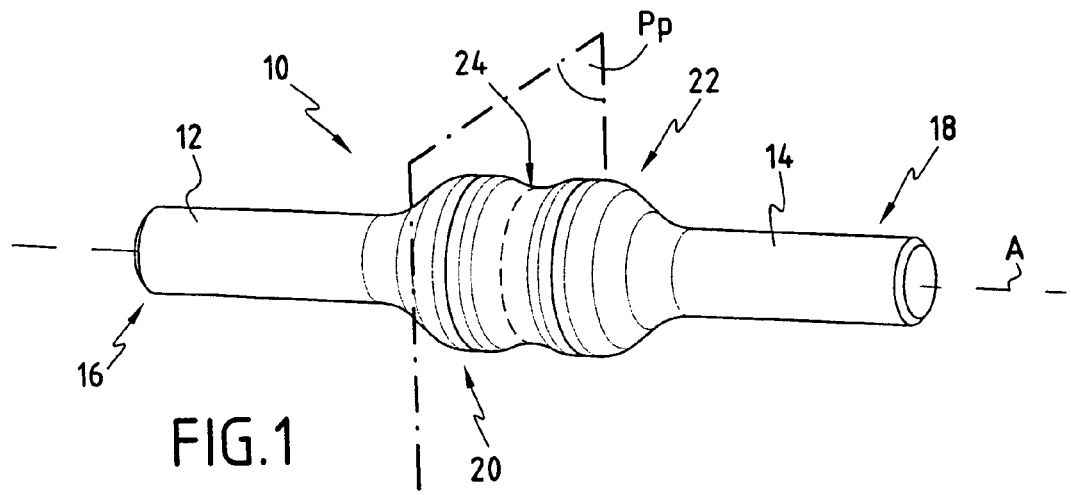
FIG. 1 is a diagrammatic perspective view of a connecting member in accordance with the invention.

The various portions of a connecting member of the invention are described initially with reference to FIG. 1.

The connecting member 10 has two cylindrical rigid parts 12 and 14. Each rigid part 12, 14 has a fixing, first portion 16, 18 and a fastening, second portion 20, 22 forming an enlargement. The facing fastening portions 20 and 22 are connected together by a connecting body 24 so that the rigid parts 12 and 14 are in axial alignment. The connecting member 10 is therefore circularly symmetrical about the axis A.

How the two rigid parts 12 and 14 are fastened together is described below with reference to FIG. 2.

The connecting body 24 is a plastics material body obtained by polymerization. The material of the body is chosen from materials which are more elastically deformable than the material of said rigid parts 12, 14 and, most importantly, whose elastic properties are of the same order of magnitude as those of the posterior ligaments that hold the spine together.

Organic silicon compounds constitute polymers whose mechanical properties can be determined by the choice of their basic components, in particular by their degree of substitution, the nature of the substituents, and their molecular weight, and whose elastic behavior predominates over its plastic behavior. They therefore constitute a family of materials suitable for interconnecting the two rigid parts 12 and 14. Also, these polymers can adhere strongly to materials of inorganic composition. Thus the connecting body 24 provides good means for fastening together the rigid parts 12, 14, which are generally made of titanium alloy.

Nevertheless, the polymer materials that can be used are not limited to organic silicon compounds, and any other material having comparable properties could be suitable.

The material of the connecting body 24 is adapted to adhere to the fastening walls 20' and 22' of said fastening second portions 20, 22. However, to increase the adhesion, openings 30, 32 are formed in the fastening walls 20, 22 of the fastening, second portions and are adapted to cooperate with asperities 26, 28 on the connecting body 24 which are inserted into the openings 30, 32.

This feature increases the contact area between the two materials and thereby increases the connecting force between them in a direction normal to said surface of contact and creates static friction forces which are additional to the adhesion force.

A connection of the above kind is obtained either by injecting the polymer while hot between the two rigid parts 12 and 14 held facing each other in a mold, or by cold molding the mixture of monomers between the two rigid parts 12 and 14, if the speed of the reaction is sufficiently low. The asperities 26, 28 are therefore formed in situ, when the polymer liquid or paste inserted into the openings 26, 28 solidifies after cooling or after a chemical reaction. Obviously, the connecting body 24 consists of the polymer disposed between the rigid parts 12 and 14, more specifically between the fastening walls 20' and 22', and, in order to retain the polymer between the facing portions while it is in the liquid state, the walls of the mold must necessarily surround the space between and in line with the two rigid parts 12, 14.

In a particular embodiment (not shown) the openings 30, 32 formed in the fastening walls 20' and 22' open onto the outside wall of the rigid parts 12 and 14 so that the liquid polymer penetrates entirely into the openings 30, 32 without it being possible for air to be trapped therein. This reinforces the fastening of the connecting body 24 to the rigid parts 12, 14.

Figure 2:
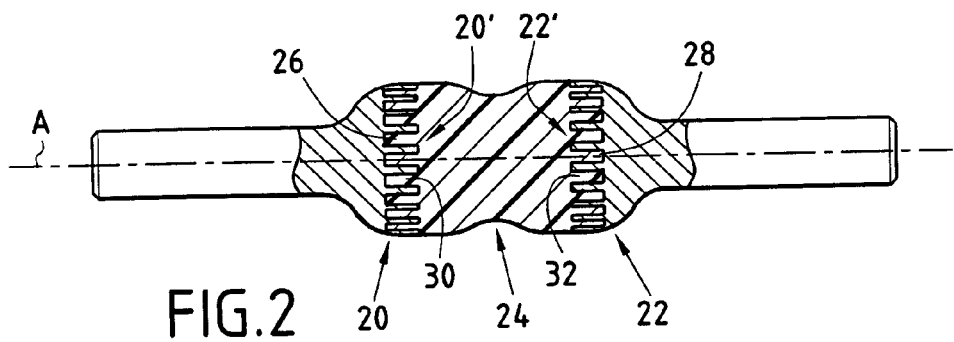
FIG. 2 is a diagrammatic view in axial section of the connecting member in accordance with the invention.

Also, the openings 30, 32, which are shown as parallel to the longitudinal axis of the connecting member in FIG. 2, can be oblique to that longitudinal axis and/or not rectilinear. These configurations increase the static friction forces of the polymer on the rigid parts, which fastens them together more strongly.

Now that the manner in which the two rigid parts are fastened together has been described, movement of the rigid parts relative to each other is described with reference to FIG. 1.

Given the circular symmetry of the rigid parts 12 and 14 and the connecting body 24, and the nature of the material of the connecting body 24, the connecting member 10 is able to bend in all directions in a plane Pp perpendicular to the axis A of the connecting member when the two first portions are immobilized. Bending of the connecting member 10 compresses one edge of the connecting body 24 and stretches the diametrally opposite edge, whereas the rigid parts 12 and 14 retain their shape. Because the material of the connecting body 24 is elastically deformable, when the stresses causing the bending are removed, the connecting member 10 returns to its original state in which the rigid parts 12 and 14 are in axial alignment.

Also, the rigid parts 12 and 14 can move relative to each other in opposite directions along the longitudinal axis A to compress or stretch the connecting body 24.

The relative movement of the two rigid parts 12 and 14 can occur in directions other than the directions described above, but the connecting member is principally loaded in bending, tension and compression, as described in more detail below.

Deformation of the connecting member connected with relative movement of the anchor members 42 and 44 is described next with reference to FIG. 3.

Figure 3:
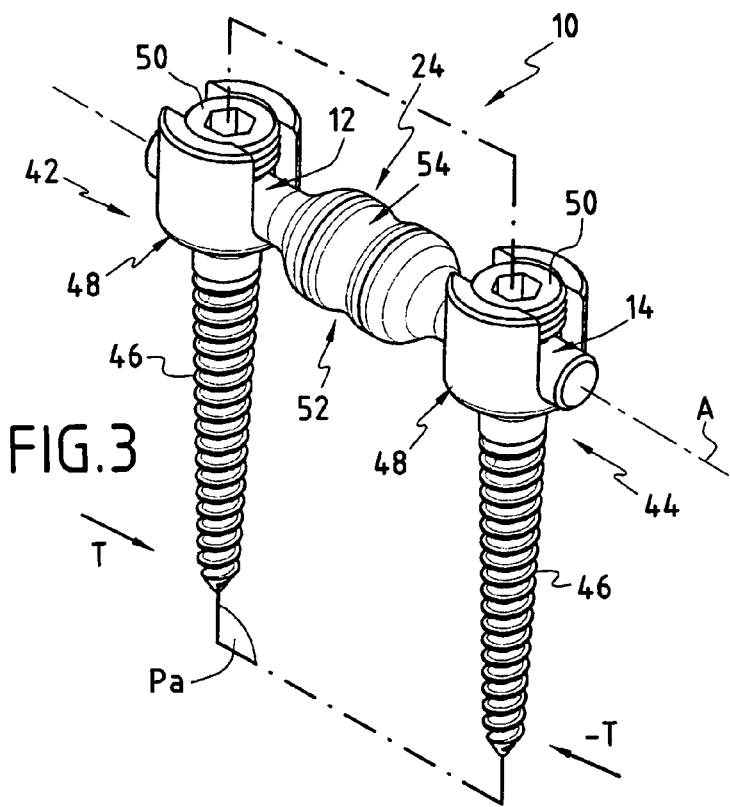
FIG. 3 is a perspective view showing anchor members connected by the connecting member.

FIG. 3 shows the connecting member 10 whose two rigid parts 12 and 14 interconnect the two anchor members 42 and 44. The two anchor members 42 and 44 are parallel to each other in a common axial plane Pa.

Each anchor member 42, 44 has a threaded shank 46 with a U-shaped head 48 at the top whose inside wall is threaded so that a screw-forming member 50 can be screwed into it. Thus the first portions 16 and 18 of the rigid parts 12 and 14 are accommodated in the heads 48 of the respective anchor members 42 and 44 and are locked to them by tightening the screw-forming members 50.

As a result, when the threaded shanks 46 of the anchor members move towards each other due to the effect of opposite forces T and −T in the plane Pa and substantially parallel to the axis A the anchor members 42 and 44 deform the connecting member, which bends.

The bending of the connecting member 10 compresses the lower edge 52 of the connecting body 24 and stretches the diametrally opposite upper edge 54, while the rigid parts 12 and 14 retain their shape. Because the material of the connecting body 24 is elastically deformable, when the stress is removed the connecting member reverts to its original rectilinear shape and the threaded shanks of the anchor members 46 return to their former relative position.

The mechanism of elastic bending of the connecting member 10 and the anchor members 42, 44 described above is the same if the threaded shanks 46 of the anchor members 42 and 44 move away from each other, the connecting member bending with the opposite curvature.

Also, the anchor members 42 and 44 are movable in translation relative to each other along the axis A, their relative movement stretching or compressing the connecting body 24.

Figure 4:
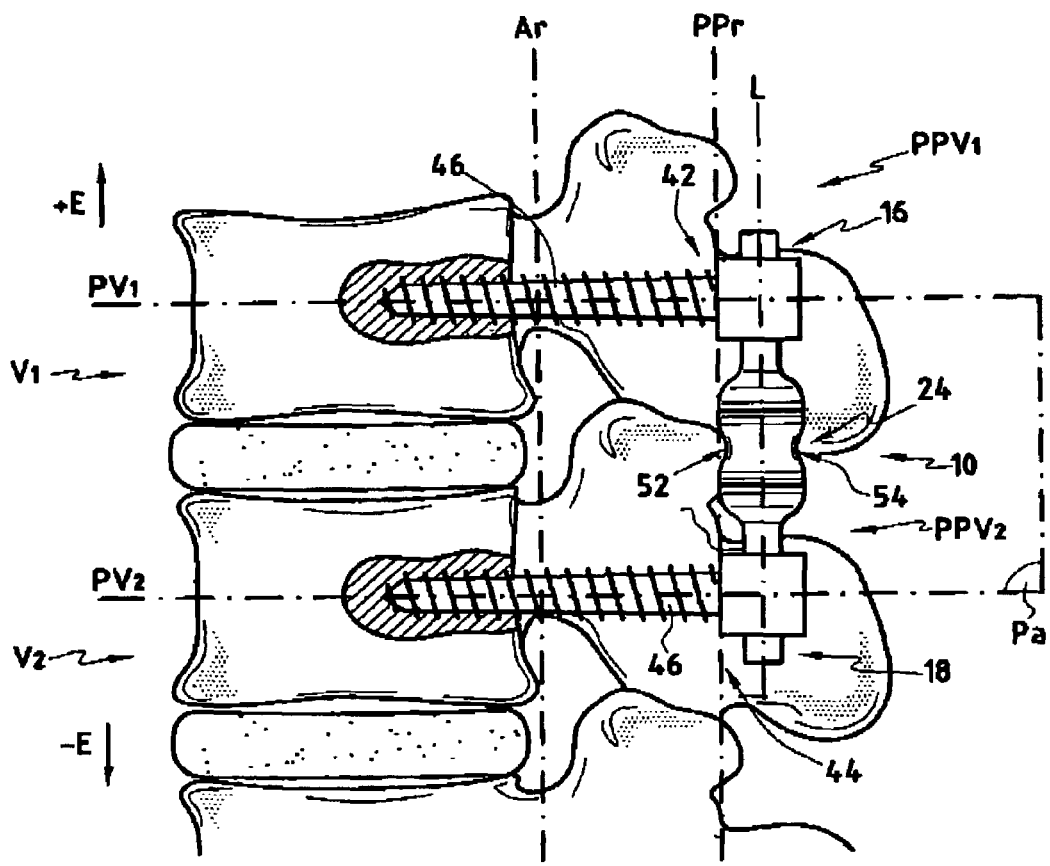
FIG. 4 is a side elevation view of a vertebral column showing two consecutive vertebrae into which there are screwed anchor members interconnected by a connecting member in accordance with the invention.

The use of the connecting member 10 in a vertebral stabilization system for fastening together at least two vertebrae V1 and V2 is described below with reference to FIG. 4.

The vertebrae V1, V2 each have respective median planes PV1, PV2 substantially perpendicular to the axis Ar of the spine of which they form part, and respective posterior walls PPV1, PPV2 defining a posterior median plane PPr of said spine.

The stabilizing system includes at least two anchor members 42 and 44 respectively screwed into the posterior walls PPV1, PPV2 of the vertebrae V1, V2, so that a line L that intersects the two anchor members 42 and 44 is substantially parallel to said axis Ar of the spine. The two first portions 16 and 18 of the connecting member 10 interconnect the two anchor members 42 and 44. As a result, the vertebrae V1 and V2, which are interconnected in their posterior portions, possess relative mobility along the axis Ar of the spine.

Thus when the spine is stretched, the vertebrae V1 and V2 move away from each other in opposite directions E and −E, which causes the threaded shanks 46 to move away from each other, deforming the connecting member 10, and in particular its connecting body 24. This is because the connecting body is compressed both longitudinally and at the upper edge 54. The deformed connecting member has it concave side facing away from the spine.

When the spine is bent, the inverse effect occurs and the vertebrae V1 and V2 move towards each other, which induces deformation of the connecting member with its concave side facing toward the spine.

The connecting body is then subjected to longitudinal extension of its upper edge 54 and possibly to compression of its lower edge 52.

It will be understood that the connecting member 10 in accordance with the invention achieves greater relative mobility of the vertebrae compared to the prior art connecting rods, which cannot be compressed longitudinally.

Figure 5:
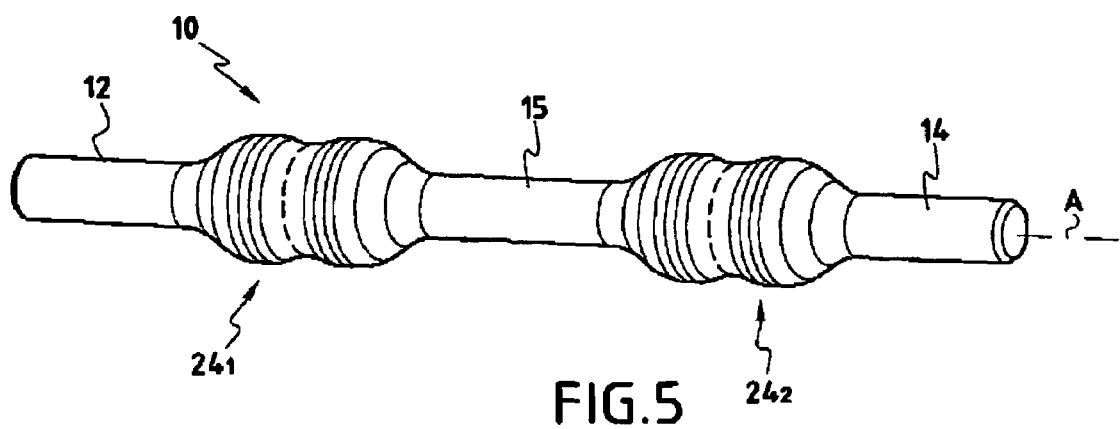
FIG. 5 is a perspective view showing a connecting member having two connecting bodies and three rigid parts of the invention.

In a particular embodiment as shown in FIG. 5, the connecting member has three rigid rod-forming parts 12, 14, 15, and two connecting bodies $24_1$, $24_2$ interconnecting the three rigid parts 12, 14, 15. To this end, the central rigid part 15 includes a fixing, first portion and two fastening, second portions, with one fastening, second portion on each side of said fixing, first portion. The fastening, second portions are connected to the two connecting bodies $24_1$, $24_2$. The other two rigid parts 12, 14, situated at the two ends of the connecting member, have a single fastening, second portion connected to the connecting bodies.

The connecting member therefore maintains the spacing between three anchor members that it interconnects, which are fixed to three substantially equidistant vertebrae, to align them. Each rigid part of the connecting member is fixed to an anchor member so that there are respective elastically deformable connecting bodies between the pairs of vertebrae. In this way, a single connecting member stabilizes three vertebrae, which reduces the time needed to assemble the stabilizing system as a whole and consequently the operating time. Also, because the three vertebrae are interconnected by a single connecting member, their mobility relative to each other is better controlled.

It goes without saying that providing connecting members having more than three rigid parts connected together by elastically deformable connecting bodies would not depart from the scope of the invention.

The invention claimed is:

1. A connecting member for stabilizing the spine and maintaining the spacing between at least two anchor members, said connecting member having a longitudinal axis and comprising:

two integrally formed rigid rod-like parts made of a first material, wherein each of said rigid rod-like parts has a first end and a second end and comprises:
a fastening portion with a plurality of openings at said first end; and
a solid cylindrical fixing portion at said second end and being insertable into an anchor member, wherein said anchor member has:
a threaded shank for screwing into a vertebra; and
a head that is oriented to receive the connecting member, wherein said solid cylindrical fixing portion is insertable into an opening of said head of said anchor member, wherein said rigid rod-like parts are aligned with each other and said fastening portions face each other, and wherein said solid cylindrical fixing portions define terminal ends of the connecting member; and
a connecting body monolithically formed from a second material, wherein the connecting body is fully disposed intermediate the two rigid rod-like parts, wherein the second material is more elastically deformable than said first material, wherein said connecting body has two ends, wherein said two ends have protrusions that mesh with said openings of the facing fastening portions, wherein said connecting body is able to deform elastically, and wherein the connecting body and the two integrally formed rigid rod-like parts are aligned along the longitudinal axis of the connecting member.

2. The connecting member of claim 1, wherein the rigid rod-like parts are mechanically connected together by only a single connecting body.

3. The connecting member of claim 1, further comprising at least an additional connecting body and at least an additional rigid rod-like part along the longitudinal axis of said member, wherein each rigid rod-like part situated between two connecting bodies has one fixing portion and two fastening portions.

4. The connecting member of claim 1, wherein each of the fastening portions of said rigid rod-like parts connected by said connecting body has a fastening wall to which said connecting body is adapted to adhere and wherein said openings are formed in the fastening walls of the fastening portions of said rigid rod-like parts.

5. The connecting member of claim 4, wherein the openings cooperate with said protrusions on said connecting body to increase the contact area between said fastening wall and said connecting body.

6. The connecting member of claim 5, wherein the asperities on said connecting body are formed in situ.

7. The connecting member of claim 5, wherein the openings of the fastening wall are parallel to the longitudinal axis of the connecting member.

8. The connecting member of claim 1, wherein the second material of said connecting body is obtained by polymerization.

9. The connecting member according to claim 1, wherein the first material of which said rigid rod-like parts are made is a titanium alloy.

10. The connecting member according to claim 1, wherein the cross-section of said rigid rod-like parts is circular.

11. A vertebral stabilization system for fastening together at least two vertebrae each having a median plane substantially perpendicular to the axis of the spine of which they are part and a posterior wall defining a posterior median plane of said spine, said system comprising:

at least two anchor members each adapted to be fixed to the posterior wall of a vertebra so that an axis which intersects said two anchor members is substantially parallel to the axis of the spine, the system further comprises:

at least one connecting member comprising:

two integrally formed rigid rod-like parts made of a first material, wherein each of said rigid rod-like parts has a first end and a second end and comprises:

a fastening portion with a plurality of openings at said first end; and a solid cylindrical fixing portion at said second end and being insertable into an anchor member, wherein said anchor member has:

a threaded shank for screwing into a vertebra; and a head that is oriented to receive the connecting member, wherein said solid cylindrical fixing portion is insertable into an opening of said head of said anchor member, wherein said rigid rod-like parts are aligned with each other and said fastening portions face each other, and wherein said solid cylindrical fixing portions define terminal ends of the connecting member; and a connecting body monolithically formed from a second material, wherein the connecting body is fully disposed intermediate the two rigid rod-like parts, wherein the second material is more elastically deformable than said first material, wherein said connecting body has two ends, wherein said two ends have protrusions that mesh with said openings of the facing fastening portions, wherein said connecting body is able to deform elastically, and wherein the connecting body and the two rigid rod-like parts are aligned along the longitudinal axis of the connecting member;

wherein the two rigid rod-like parts of the connecting member interconnect said two anchor members so that the axis of said connecting member is substantially parallel to the axis of the spine, wherein said vertebrae, which are interconnected via their posterior portions, present relative mobility along said axis of said spine.

* * * * *